United States Patent
Moore et al.

(10) Patent No.: US 12,280,163 B2
(45) Date of Patent: Apr. 22, 2025

(54) UV MODULE, SYSTEM, AND METHOD FOR DEACTIVATING BIOLOGICALLY CONTAMINATED SURFACES IN AN INTERIOR OF A DEVICE

(71) Applicant: Analytic Jena GmbH+Co. KG, Jena (DE)

(72) Inventors: Thomas Moore, Jena-Drackendorf (DE); Claus Knippschild, Jena (DE); Martin Hentschel, Jena (DE)

(73) Assignee: Analytik Jena GmbH+Co. KG, Jena (DE)

( * ) Notice: Subject to any disclaimer, the term of this patent is extended or adjusted under 35 U.S.C. 154(b) by 799 days.

(21) Appl. No.: 17/406,877

(22) Filed: Aug. 19, 2021

(65) Prior Publication Data
US 2022/0054677 A1    Feb. 24, 2022

(30) Foreign Application Priority Data

Aug. 19, 2020  (DE) .................... 10 2020 121 809.5
Aug. 21, 2020  (DE) .................... 10 2020 121 995.4

(51) Int. Cl.
*A61L 2/10*      (2006.01)
*B01L 7/00*      (2006.01)
*C12Q 1/686*     (2018.01)

(52) U.S. Cl.
CPC ............ *A61L 2/10* (2013.01); *A61L 2202/11* (2013.01); *A61L 2202/14* (2013.01)

(58) Field of Classification Search
None
See application file for complete search history.

(56) References Cited

U.S. PATENT DOCUMENTS

2011/0305597 A1    12/2011  Farren
2013/0277574 A1*   10/2013  Dayton ................ A61L 2/10
                                             250/455.11

(Continued)

FOREIGN PATENT DOCUMENTS

CN    107921158 A    4/2018
CN    110975958 A    4/2020

(Continued)

OTHER PUBLICATIONS

Document titled CN111321074A Real-time reaction thermal cycle device with air guide structure in PCR reaction container, machine translation of CN111321074A provided by EPO, original document published 2020 (Year: 2020).*

*Primary Examiner* — Holly Kipouros
(74) *Attorney, Agent, or Firm* — Christopher R. Powers; Endress+Hauser (USA) Holding, Inc.

(57) ABSTRACT

A UV module for deactivating biologically contaminated surfaces in an interior of a device includes: a carrier; a radiation source affixed to the carrier and configured to emit UV radiation; and a control unit connected to the radiation source, wherein the control unit is configured to receive and process at least one information item to activate the radiation source to emit UV radiation based on the at least one information item. A system comprises such a UV module wherein the device is configured for the handling and/or examination of samples comprising biological material and has an interior into which the UV module can be introduced. A method for deactivating biologically contaminated surfaces in an interior of a device for the handling and/or examination of samples comprising biological material includes using the device.

25 Claims, 3 Drawing Sheets

(56) References Cited

U.S. PATENT DOCUMENTS

| | | |
|---|---|---|
| 2015/0209457 A1 | 7/2015 | Bonutti et al. |
| 2017/0340760 A1 | 11/2017 | Starkweather et al. |
| 2018/0113066 A1* | 4/2018 | Freitag .................. A61L 2/10 |
| 2018/0193831 A1* | 7/2018 | Hopper .................. F04B 43/00 |
| 2018/0357385 A1* | 12/2018 | LaPorte .................. A61L 2/08 |
| 2019/0117811 A1 | 4/2019 | Barber, III |
| 2019/0209718 A1 | 7/2019 | Church et al. |
| 2019/0298871 A1* | 10/2019 | Dobrinsky .............. A61L 2/10 |
| 2019/0365937 A1 | 12/2019 | Lamoureux |
| 2020/0147249 A1 | 5/2020 | Hussein et al. |
| 2020/0150138 A1 | 5/2020 | Buller et al. |
| 2020/0179543 A1 | 6/2020 | Deshays et al. |
| 2022/0016437 A1* | 1/2022 | Jarausch .................. A61L 2/24 |

FOREIGN PATENT DOCUMENTS

| | | | |
|---|---|---|---|
| CN | 110975959 A | | 4/2020 |
| CN | 111201044 A | | 5/2020 |
| CN | 111321074 A | * | 6/2020 |
| DE | 102018000575 A1 | | 7/2019 |
| DE | 102018124408 A1 | | 4/2020 |
| DE | 102018124412 A1 | | 4/2020 |
| GB | 2565865 A | | 2/2019 |
| WO | 2011031167 A1 | | 3/2011 |
| WO | 2017020028 A1 | | 2/2017 |
| WO | 2018074971 A1 | | 4/2018 |
| WO | 2020148322 A1 | | 7/2020 |

\* cited by examiner

UV MODULE, SYSTEM, AND METHOD FOR DEACTIVATING BIOLOGICALLY CONTAMINATED SURFACES IN AN INTERIOR OF A DEVICE

CROSS-REFERENCE TO RELATED APPLICATION

The present application is related to and claims the priority benefit of German Patent Application No. 10 2020 121 809.5, filed on Aug. 19, 2020, and German Patent Application No. 10 2020 121 995.4, filed on Aug. 21, 2020, the entire contents of which are incorporated herein by reference.

TECHNICAL FIELD

The present disclosure relates to a UV module for deactivating biologically contaminated surfaces in an interior of a device; to a system having a device and a UV module which serves to deactivate biologically contaminated surfaces in an interior of the device; and to a method for deactivating biologically contaminated surfaces in an interior of a device, for example, for handling and/or examining samples comprising biological material.

BACKGROUND

In laboratory analysis, especially in the life science field and in medical diagnostics, samples comprising biological material are examined in many instances. Laboratory devices are thereby used that have an interior, for example, a sample chamber, into which the samples are positioned for analysis or for preparation of an analysis, for example, for a pretreatment for comminution, purification, homogenization, or enrichment. Examples of such interior spaces serving for the accommodation and treatment and/or analysis of samples are scales, mills, mortars, automatic pipetting machines, thermocyclers, or real-time thermocyclers.

The samples are often handled in sample vessels of plastic material, for example, individual sample tubes or what are known as wells of microtiter plates having a plurality of sample vessels, and positioned in an interior, e.g., a sample chamber, in the laboratory devices. Such sample containers are closed off by caps, lids, and adhesive films. Various laboratory devices have mechanical receptacles which force an exact positioning of the sample vessels that are used. In many devices, the sample chamber is closed manually or automatically to be able to execute a treatment of the samples or execute measurements. A thermocycler with a sample chamber that can be automatically closed off by a cover is known from DE 10 2018 124 408 A1 or DE 10 2018 124 412 A1.

Many of the tasks take place manually or in an (at least partially) automated manner, and there is no active monitoring with regard to the sealing tightness of the sample vessel. Thus, given all of these tasks there is the risk that sample material is carried over and/or contaminates surfaces of devices inserted into interior spaces. Aerosols which are swirled through the air and deposit in the interior spaces are thereby also of particular importance. The interior spaces are often not sufficiently accessible for cleaning or ventilation, so that a disinfection by wiping is difficult to perform.

UV (i.e., ultraviolet) radiation is conventionally used for the deactivation of biologically contaminated surfaces, for example, contaminated by fungi, bacteria, and viruses, or also of contaminated media such as water. The UV radiation produces modifications of the original binding state of various molecular building blocks in the nucleic acids. Due to irradiation with UV radiation, the nucleus of microorganisms can therefore be altered in such a way that cell division is no longer possible, or that viruses can no longer reprogram cells. As a result, the microorganisms or viruses can no longer propagate or be propagated. UV radiation is also used in laboratory operation for deactivating contaminated devices, surfaces or volumes. The applicant offers, for example, cabinets and workstations for sample preparation for polymerase chain reaction (PCR) in which the risk of sample carryover can be considerably reduced by means of a combination of filters and UV radiation. The UV source is arranged within the cabinet or the workstation and can be used for decontaminating the interior enclosed by the cabinet or the workstation. To avoid an inadvertent irradiation of the samples, a key serves to turn on the UV source. The UV source used in these devices consists of one or more UV tubes arranged in the ceiling region of the cabinet or workstation.

Entire laboratory rooms are also illuminated with UV-C radiation, for example, at night, and their air is circulated through filter systems, which can also be equipped internally with additional UV-C radiation sources. A significant practical problem is thereby the optical shadowing and/or too little aeration of surfaces or volumes. Especially surfaces in interior spaces of devices of laboratory equipment, such as thermocyclers, laboratory scales, automatic extraction machines, or non-accessible robotic systems, cannot be reached with these means, and existing biological contaminants cannot be deactivated, with sufficient certainty.

Because of the effect of UV-C radiation, which changes the DNA or RNA of cells or viruses, the use of such radiation for decontamination in process or laboratory operation requires additional protective measures to not endanger persons who deal with the corresponding devices.

To decontaminate a InnuPure C16™ automatic extraction machine, which is manufactured and sold by Applicant, Applicant further offers a decontamination module comprising a UV lamp. The decontamination module can be placed into a drawer of the automatic extraction machine, which is intended for receiving samples, and be inserted into the sample chamber to be decontaminated. If the decontamination module is correctly positioned in the automatic extraction machine, a safety switch rests against the device wall in such a way that it closes the electric circuit for supplying power to the UV lamp. In addition, a further pushbutton must be actuated to activate the UV lamp. In this way, an unintentional activation of the UV lamp is prevented, especially if the module is not yet correctly positioned in the device.

SUMMARY

The object of the present disclosure is to provide a further improved device and a method for the safe deactivation of biologically contaminated surfaces in interior spaces of devices.

This object is achieved according to the present disclosure by the UV module, the system and the method according to present disclosure. Advantageous embodiments of each are listed in the dependent claims.

The UV module according to the present disclosure for deactivating biologically contaminated surfaces in an interior of a device comprises: a carrier; at least one radiation source, which is affixed to the carrier and is designed to emit UV radiation; and a control unit connected to the at least one radiation source, wherein the control unit is configured to receive and process at least one information item to operate, for example, activate, the radiation source for emitting UV radiation based on the at least one information item.

The UV module may be configured to be inserted into the interior of a device to deactivate contaminated surfaces in the interior. The deactivation of biologically contaminated surfaces is understood here and in the following to mean the neutralization, as described above, of microorganisms, for example, fungi, bacteria, algae, and/or viruses, present on the surfaces. The neutralization by means of UV radiation is based on the already mentioned alteration of the DNA or RNA, which leads to the situation that the microorganisms or viruses are incapable of propagating or being propagated. This is also colloquially referred to as "decontamination." However, the technical term of decontamination of biologically contaminated surfaces often also involves the removal of contamination via cleaning measures, for example, via wipe disinfection. The deactivation or decontamination of an interior in a device by means of a UV module, as described here, may but need not include such a further cleaning.

The control unit can, for example, be an electrical or electronic circuit which has a logic unit which is configured for processing the information. The logic unit may comprise a logic circuit, for example based on Boolean algebra, or a more complex computing unit, for example, a microprocessor. In that the control unit operates the radiation source based on the at least one information item, e.g., to activate the radiation source for the emission of UV radiation or to excite it to emit UV radiation, it is possible to reliably prevent unauthorized or unintentional operation of the at least one radiation source. While the function of a safety switch, as provided in the decontamination module described above according to the prior art, can be bypassed by misuse, the transmission to the control unit of information on the basis of which the control unit operates the radiation source can serve to enable the radiation source to be activated on only if the operation of the radiation source is sufficiently safe or is authorized based on certain specifications. An improper or inadvertent intervention in the transmission of the information to the control unit can be prevented more easily than the bypassing of a mechanical safety switch.

In an advantageous embodiment, the at least one radiation source can comprise a UV-LED configured to emit radiation in the UV-B or UV-C spectral range. The UV-B spectral range is thereby understood to be the spectral range between 280 nm and 315 nm; the UV-C spectral range is understood to be the spectral range between 100 nm and 280 nm. The UV-LED advantageously emits radiation of one or more wavelengths in the range between 100 and 380 nm, preferably between 200 and 310 nm, or further preferably between 250 and 280 nm, for example, at 278 nm with a half-width of approximately 10 nm. In an advantageous embodiment, the UV module can have a plurality, for example, a multiplicity of UV-LEDs. These can advantageously be arranged on the carrier of the UV module in such a way that they radiate in a plurality of different spatial directions so as to illuminate an interior of a device, into which the UV module is inserted, essentially completely and without shadows, with a radiation dose sufficient for deactivation. In contrast, the mercury-containing lamps that are normally used in the prior art for deactivating microorganisms or viruses are to be assessed critically for environmental and occupational safety reasons. In the meantime, laws and guidelines in many countries also provide for avoiding mercury in process and laboratory equipment. An example of such a requirement is the RoHS guideline of the EU. In contrast to such classical UV light sources, UV-LEDs are more compact, energy-efficient, very flexible to use, and do not require a long warm-up phase.

The at least one information item on the basis of which the control unit operates the radiation source can, for example, be transmitted to the control unit by a device into which the UV module is inserted. The device can thus signal to the control unit, by means of the information transmitted to the UV module, that the activation or operation of the at least one radiation source is safe. The device can, for example, be configured to transmit the at least one information item when the device is in a predefined, for example, a safe, operating state for activating or operating the at least one radiation source. Such a safe operating state can, for example, be present when the interior in which the UV module is arranged for deactivating biological harmful substances present there, for example, microorganisms or viruses, is completely closed off from the environment so that no harmful UV radiation, which is hazardous to users or laboratory personnel, can escape from the interior to the outside.

In a further advantageous embodiment, the UV module comprises at least one sensor, as nonlimiting examples, a radiation detector, a movement sensor, a position sensor, a camera or a temperature sensor, wherein the sensor is connected to the control unit to transmit this one measurement signal as the at least one information item. For example, the sensor can serve to determine whether the device is in the safe operating state for activating or operating the at least one radiation source and/or whether the UV module is arranged correctly within the interior to be decontaminated. For example, if the UV module is intended to decontaminate an interior of a device designed to be light-tight, e.g., an interior of a thermocycler or of a qPCR thermocycler in which optical measurements are performed according to specification, the sensor may comprise a radiation detector or a daylight sensor. In such an embodiment, the sensor signal can be used to determine, for example by means of a target or threshold value comparison, whether the interior in which the UV module is located is closed off and thus dark. The control unit of the UV module can, for example, be configured to perform a threshold comparison of the sensor signal with a predefined threshold value corresponding to the sensor signal when the interior is closed, and to activate the at least one radiation source depending on the comparison.

In a further advantageous embodiment, the UV module can have at least one temperature control element, for example at least one Peltier element, which can be affixed to the carrier, for example. The at least one temperature control element can be designed for heating and/or cooling. With regard to the at least one radiation source, it can be arranged such that it can cool the radiation source during operation. The operation of the at least one cooling element can be controllable via the control unit of the UV module.

In order to dissipate heat from the at least one radiation source, in an alternative embodiment the UV module can have thermal contact surfaces which can be placed on a temperature control device of the device into which the UV module is to be inserted. A UV module designed in this way can, for example, be used in a sample chamber of a thermocycler such that the thermal contact surfaces rest against a temperature control block of the thermocycler, which in PCR operation is provided for temperature control of the samples.

In a further embodiment, the UV module can have a battery, for example, a battery that is rechargeable without contact, which is connected to the control unit and/or the at least one sensor as a voltage source. The power provided by the rechargeable battery can be used for operating the control unit, the optionally present at least one sensor, and/or the radiation source. Alternatively, the UV module can be connected to the device by means of a cable or a flexible printed circuit board in order to be supplied with power therefrom. The UV module can also be designed to be supplied with power from an external power supply, for example, the device, in a contactless manner, for example, via an inductive interface. For this purpose, it can have a coil which is configured for receiving power and is connected to the components to be supplied with power, for example, the at least one radiation source, the control unit, and the at least one sensor.

In a further embodiment, the control unit can have an interface for contactless communication, for example, according to a Bluetooth, NFC (near-field communication), RFID (radio frequency identification), or radio standard, or means for optical communication, e.g., a modulatable light source and a light receiver. This interface can serve to receive the at least one information item.

In a further embodiment, the UV module can comprise a drive unit, for example a motor, which can be controlled by the control unit. The drive unit can be used to provide mechanical functions within an interior of a device, for example in order to manipulate a consumable module (technical term: consumable) within the interior, for example to move, unlock, or lift it out of an original position. For this purpose, the UV module can have a mechanical manipulator, for example a plunger or a tilting mechanism, connected to the drive unit. The motor can be supplied with power from the previously mentioned rechargeable battery of the UV module, or via a separate power source, for example a power supply of the device into which the UV module is inserted, which can be connected to the UV module.

The present disclosure also encompasses a system comprising at least the following components: a device for handling and/or examining samples comprising biological material, having an interior; and a UV module that can be introduced into the interior, according to any of the embodiments described in the preceding for deactivating biologically contaminated surfaces in the interior.

In an advantageous embodiment, the device can have a logic unit which is configured to transmit the at least one information item to the control unit, for example in the form of a signal, for example, a digital signal. The logic unit may comprise a logic circuit, for example based on Boolean Algebra, or a more complex computing unit, which is suitable for executing both logical and arithmetic operations. The computing unit may comprise a microprocessor, for example. The at least one information item transmitted from the logic unit to the control unit can be a control command which the control unit executes by activating the at least one radiation source. The at least one information item can also be a measured value or information derived from a measured value, an identifier, a security ID, a password, an authentication information, or a security token. For example, the logic unit may be configured to transmit a particular identifier or authentication information or a token to the control unit of the UV module only if the device is in a predefined operating state. Thus, the authentication information or identifier can simultaneously serve for authenticating the device and for checking or ensuring the presence of the predefined operating state via the control unit of the UV module.

The at least one information item can comprise a plurality of individual information items; for example, the logic unit can send authentication information, for example, an identifier, a token or a password, and additionally send a control command, wherein the control unit first authenticates the logic unit as a source of the control command on the basis of the authentication information and only executes the control command after successful authentication.

In a further embodiment, the logic unit can be configured to transmit the at least one information item to the control unit when the device is in a predefined, safe operating state. The predefined operating state of the device can, for example, be a state which is safer for the deactivation by means of UV radiation, in which the interior of the device to be decontaminated is closed off such that no harmful UV radiation can escape from the interior to the outside. The operating state can also be a dedicated cleaning or decontamination operating state of the device. For example, if the predefined operating state includes that a cover, for example, a door or a lid, of the interior is completely closed, the logic unit can determine the presence of the operating state on the basis of a signal from a cover sensor, for example a microswitch, a movement sensor, or a proximity switch, which detects the closure of the cover, and output the at least one information item to the control unit based on the signal of the cover sensor. Alternatively, the logic unit can automatically determine the presence of the operating state on the basis of internal data of the device, for example on the basis of control information of an automatic cover closing mechanism.

In a further embodiment, the logic unit and the control unit can be connected to one another for wireless communication, for example, according to a Bluetooth standard, NFC standard, RFID standard, by means of radio, or by means of optical communication. The logic unit and the control unit can also be connected to one another for line-bound communication, for example via cables or a flexible circuit board and a plug-in connector.

For this purpose, the control unit can be configured to authenticate the logic unit on the basis of the at least one information item and to activate the radiation source for the emission of UV radiation only after successful authentication. This can occur by means of a hardware or software token, for example. It is possible that the logic unit transmits the information to the control unit only when the device is in a state which is safe for deactivating the interior by means of UV radiation, for example when the interior is completely closed such that no UV radiation escapes to the outside.

The logic unit can be configured to authenticate the control unit and to transmit the at least one information item to the control unit only after successful authentication. This can occur by means of a hardware or software token, for example.

The interior can be designed to be closed off after the introduction or via the introduction of the UV module such that no UV radiation can escape from the interior to the outside. For example, the device can have a cover, for example, a door or a lid, which closes off the interior space after the introduction of the UV module in a light-tight manner and which can be closed off after the introduction of the UV module. Alternatively, the UV module can be introduced into the interior in such a way that a side wall of the UV module produces a light-tight covering of the interior.

In a further embodiment, the system can comprise a sensor, for example, arranged on the UV module, that is configured to provide a measurement signal on the basis of which it can be determined whether the device is in the safe operating state for activating or operating the at least one radiation source, and/or whether the UV module is arranged correctly inside the interior to be decontaminated. For example, the measurement signal can be used to determine whether the interior is closed off. This sensor can be, for example, a light sensor, the aforementioned cover sensor, a camera, or a light barrier. If the sensor is arranged on the UV module, in addition to providing the at least one information item transmitted by the device or the logic unit of the device, it can provide additional, redundant information for the control unit on the basis of which the control unit operates, e.g., activates, the radiation source. For example, the control unit can be configured to activate the at least one radiation source for the emission of UV radiation only when it receives from the logic unit of the device a first information item which signals a predefined, safe operating state of the device, e.g., the closed state of the interior, and if it additionally receives from the at least one sensor a second information item which signals the predefined, safe, operating state of the device.

In a further embodiment, the at least one information item, for whose reception and processing the control unit is configured to activate the radiation source for the emission of UV radiation based on said information, can comprise the measurement signal of this sensor or information derived from the measurement signal. For example, the control unit can receive the measurement signal of the sensor to derive therefrom whether the interior is closed off completely, for example, in a light-tight manner. For this purpose, the control unit can be configured to perform a comparison of the measurement signal, or of a value derived therefrom, with a target signal or a target value or a threshold value that represents the predefined, safe operating state of the device, e.g., the completely closed state of the interior. In this embodiment, the control unit does not necessarily need to receive a signal from the logic unit of the device to activate the radiation source for the emission of UV radiation. Rather, it can be configured to control the radiation source solely on the basis of the measurement signal of the sensor. A higher operational safety is achieved, however, if the control unit also receives information from the logic unit of the device, on the basis of which it operates the radiation source.

In a further embodiment, the logic unit of the device can receive and evaluate the measurement signal of the at least one sensor. The logic unit can, for example, be configured to determine, on the basis of the sensor signal, whether the device is in a predefined operating state, for example safe for the deactivation of the interior by means of UV radiation, e.g. whether the interior is completely closed such that no UV radiation escapes to the outside. For this purpose, the logic unit can be configured to compare the sensor signal or a value derived therefrom with a target signal representing the safe state, or with a target or threshold value. The logic unit can be further configured to transmit the at least one information item to the control unit, on the basis of which the control unit operates the radiation source, for example, activates it, when the sensor signal or the value derived therefrom corresponds to the predefined operating state, e.g., the safe operating state of the device. To ensure greater safety, at least one further sensor, e.g., a redundant sensor, can be provided in the device and/or at the UV module, which further sensor provides the logic unit and/or the control unit with a further measurement signal from which it can be derived whether the device is in a safe operating state for the deactivation of the interior by means of UV radiation.

The UV module can have a temperature sensor and/or an acceleration sensor and/or a position sensor and/or a camera, wherein the at least one information item, for the reception and processing of which the control unit is configured to activate the radiation source for the emission of UV radiation based on said information item, comprises the measurement signals of the temperature sensor and/or of the acceleration sensor and/or of the position sensor, or information derived from one or more of these measurement signals.

The device can be a device used in process or laboratory analysis, e.g. a measuring device, a device for carrying out a liquid handling method, or a device for the preparation of samples which contain biological material. The device can be, for example, a laboratory scale; a spectrometer; an incubator; a liquid handling system with an integrated transport device; a thermocycler, for example a qPCR thermocycler; or a robotic system with a housing closed off from the outside.

The device can have means for temperature control, for example, cooling, of the at least one UV radiation source, e.g., Peltier elements which can be controlled by the device.

In an advantageous embodiment, the device is a thermocycler or a qPCR thermocycler. In this instance, the carrier of the UV module can have substantially the same dimensions as a conventional microtiter plate that is to be inserted into the thermocycler (technical term: sample tray) and, to execute a decontamination, can be inserted instead of the microtiter plate into the sample chamber of the thermocycler. In this embodiment, the at least one radiation source advantageously has one or more UV-LEDs, for example, a plurality of UV-LEDs. A heating and cooling device of the thermocycler, for example a temperature control block which, in normal operation, serves to adjust the temperature profile required for the PCR, can serve for cooling the at least one radiation source. For example, the thermocycler, for example, a logic unit integrated into the thermocycler, can be placed in a decontamination operating state when the UV module is inserted into the sample chamber. In the decontamination operating state, the thermocycler or the logic unit, for example, an integrated logic unit of the thermocycler, can be configured to register the presence of a safe operating state on the basis of sensor or control signals, e.g., whether a cover or a lid of the sample chamber is sealed in a light-tight manner. If this requirement is present, the logic unit can be further configured to transmit the at least one information item, for example a control command, authentication information, a token, an identifier, or a password, to the control unit of the UV module, on the basis of which information item the control unit of the UV module activates the radiation source. In the decontamination operating state, the thermocycler can be further configured to cool the UV radiation source of the UV module by means of the heating and cooling device.

The UV module or the device may moreover have a timer using which the control unit deactivates the radiation source after a predefined time interval has elapsed.

As already described, the UV module can comprise a drive, for example a motor, which can be controlled, for example, by the control unit, as well as a manipulator connected to the drive, for example a push rod or a tilting mechanism. The drive can be used to provide mechanical functions within an interior of the device, for example in order to manipulate a consumable module (technical term:

consumable) within the interior, for example to move, unlock, or lift it out of an original position. The motor can be supplied with power from a rechargeable battery of the UV module or via a separate power source, for example a power supply of the device in which the UV module is used and which can be connected to the UV module.

The present disclosure further encompasses a method for deactivating biologically contaminated surfaces in an interior of a device, for example, for the handling and/or examination of samples comprising biological material. This method includes: introducing into the interior a UV module having at least one radiation source designed for emitting UV radiation; receiving at least one information item via a control unit of the UV module; and processing the at least one information item via the control unit, and operating, for example, activating, the radiation source for the emission of UV radiation via the control unit.

The method and/or one of the method embodiments described below can be executed by means of the UV module described above or by means of the system described above.

The method can further include irradiating the biologically contaminated surfaces in the interior with the UV radiation emitted by the radiation source, for example, over a predefined period of time. For this purpose, the control unit can have a timer.

The device may include a logic unit, wherein the method further comprises: transmitting the at least information item from the logic unit to the control unit, wherein the at least one information item may comprise a control command and/or authentication information.

In an advantageous method embodiment, the logic unit transmits the information only when the device is in a predefined operating state, for example, in an operating state that is safe for the deactivation of the interior, in which the interior is closed off in such a way that no UV radiation travels from the interior to the outside. If the at least one information item transmitted from the logic unit to the control unit is a sensor signal or a value derived therefrom, the information can alternatively also be transmitted from the logic unit to the control unit of the UV module at regular time intervals. In such an embodiment, the control unit can check based on the transmitted information whether the predefined operating state of the device is present and operate or activate the radiation source depending on the test result.

At least during a period of time within which the radiation source emits UV radiation, it can be cooled by means of a temperature control device which, for example, can comprise at least one Peltier element. The cooling can be controlled by the control unit and/or by a logic unit of the device. If the device is a thermocycler or qPCR thermocycler, this can cool the radiation source by means of a heating and cooling device integrated into the thermocycler. For this purpose, the thermocycler can execute a decontamination program that is executable by the logic unit.

The UV module can have at least one sensor, for example, a radiation detector, a movement sensor, a position sensor, a camera, or a temperature sensor, which is connected to the control unit in order to transmit to this a measurement signal as the at least one information item, and wherein the method further comprises transmitting the measurement signal of the at least one sensor to the control unit. On the basis of the measurement signal of the sensor, the control unit can check the plausibility of the at least one information item received by the logic unit of the device. It can also use the sensor signal as redundant information about the presence of an operationally safe state of the interior to be deactivated, in order to provide additional safety.

For example, the control unit can receive first information from the logic unit and receive second information from the at least one sensor, wherein the control unit activates the radiation source only if it is determined from both information items, based on predefined criteria, that the device is in a predefined operating state, e.g., that the interior is closed off in such a way that UV radiation does not travel from the interior to the outside.

BRIEF DESCRIPTION OF THE DRAWINGS

The present disclosure is explained in greater detail below based on the exemplary embodiments shown in Figures. Shown are.

DETAILED DESCRIPTION

Figure 1:
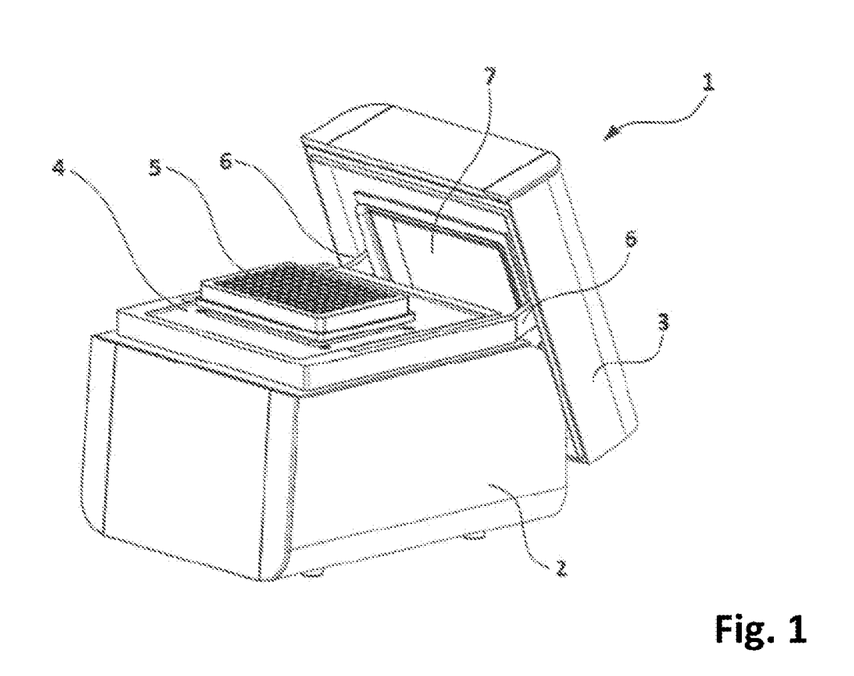
FIG. 1 shows a perspective view of a thermocycler having a sample chamber for receiving samples containing biological material.

Schematically shown in FIG. 1 is a thermocycler 1, known from DE 10 2018 124 408 A1 or DE 10 2018 124 412 A1, for the thermal treatment of samples for performing a polymerase chain reaction (PCR). The use of a UV module according to the present disclosure for deactivating surfaces in an interior of a device is explained in more detail in the following by way of example with reference to this thermocycler. The thermocycler 1 has a base unit 2 and a lid 3. The base unit 2 has a receiving region 4 in which a temperature-control block is located. Reaction vessels in which samples to be thermally treated are located can be arranged in the receiving region 4. In the exemplary embodiment shown here, the reaction vessels are formed in a rectangular microtiter plate 5 arranged in the receiving region 4. Such microtiter plates are typically made of plastic. The lid 3 is connected to the base unit 2 via two connecting arms 6. The connecting arms 6 are coupled to a lid drive, which is arranged in the base unit 2 and can move the lid 3 to automatically open and close the base unit 2. Arranged in the lid 3 is a cover plate 7 whose front surface points towards the receiving region 4 and is intended to bear against the reaction vessels formed in the microtiter plate 5 when the lid 3 is closed. In the exemplary embodiment described here, the cover plate 7 is designed to be heatable. If the lid 3 is closed, a sample chamber that surrounds the sample receptacle is formed between the base unit 2 and the lid 3.

Figure 2:
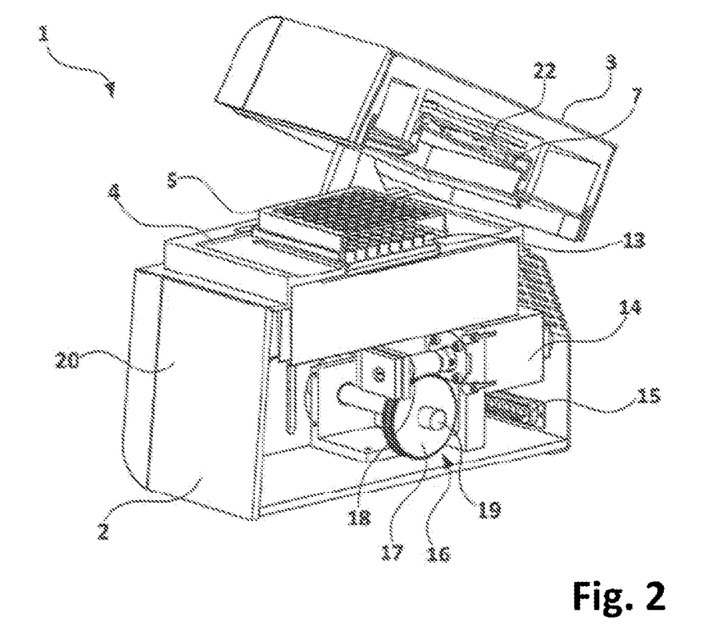
FIG. 2 shows a cross-sectional view of the thermocycler shown in FIG. 1.

The thermocycler 1 shown in FIG. 1 is visible in FIG. 2 in a cross-sectional view. Visible here are the lid drive accommodated in the housing 20 of the base unit 2 for the automatic closure of the lid 3, and a temperature control block 13 for temperature control of the samples. The lid drive comprises a controllable motor 14, for example an electric motor, which can be connected to a controller arranged in the base unit 2 itself or outside of the base unit 2, for example an electronic control circuit which can optionally comprise a CPU. The controller serves inter alia as a drive controller of the thermocycler 1. An interface 15 is provided in the base unit for connecting the motor 14 or the internal controller of the thermocycler 1 to a controller external to the device. In the present example, the lid drive further comprises a gear system 16 which can be actuated by the motor 14. In the present example, the gear system 16 comprises a gear wheel 17 and a helical worm shaft 18 whose rotational movement causes the gear wheel 17 to rotate. The gear wheel 17 is rigidly connected to the drive shaft 19, which is connected via a guide to the connecting arms 6 in order to drive the movement of the lid 3.

The design of the lid 3 is also visible in detail in the cross-sectional view of FIG. 2. The lid 3 contains a cover plate 7 which can be heated by means of a heating module. This is coupled to a contact pressure plate 22 via compression springs. The force exerted by the lid drive on the connecting arms 6 and the contact pressure plate 22 is transmitted to the cover plate 7 via the compression springs.

For alternately heating and cooling the samples to perform a plurality of PCR cycles, the thermocycler 1 has a temperature control module comprising a temperature control block 13. The temperature control block 13 is made of a metal having high thermal conductivity, for example silver or aluminum, and has a plurality of receptacles for reaction vessels. In the present example, the microtiter plate 5 is placed on the temperature control block 13 in such a way that the depressions formed in the microtiter plate and serving as reaction vessels project into the receptacles. In the example shown here, the receptacles are designed as cylinders which are situated upright on a base surface of the temperature control block 13. Arranged on the underside of the temperature control block 13 are temperature control elements, for example Peltier elements, which are in contact with a heat sink. The regulation of the temperature of the temperature control block 13 can likewise be executed by the controller or by a separate control unit.

As described above, a UV module can be used for deactivating possibly biologically contaminated surfaces within the sample chamber of the thermocycler described here by way of example, as will be described in more detail below.

Figure 3A:
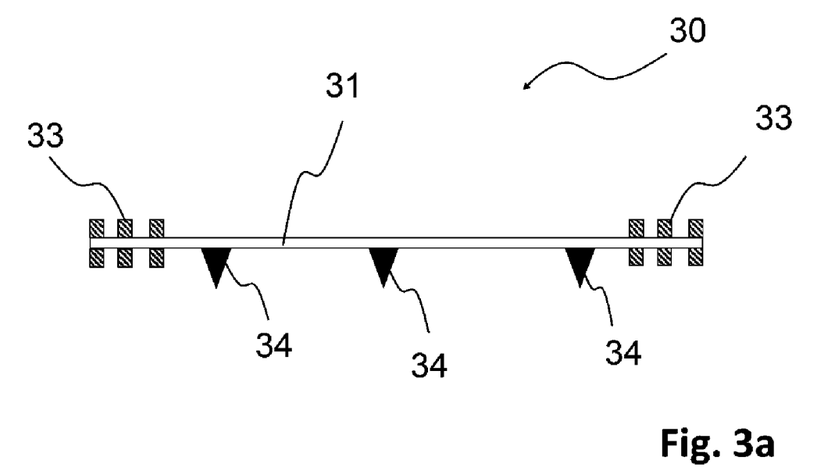
FIG. 3a shows a side view schematic illustration of a UV module according to a first exemplary embodiment of the present disclosure for decontaminating the sample chamber of the thermocycler depicted using FIGS. 1 and 2.
Figure 3B:
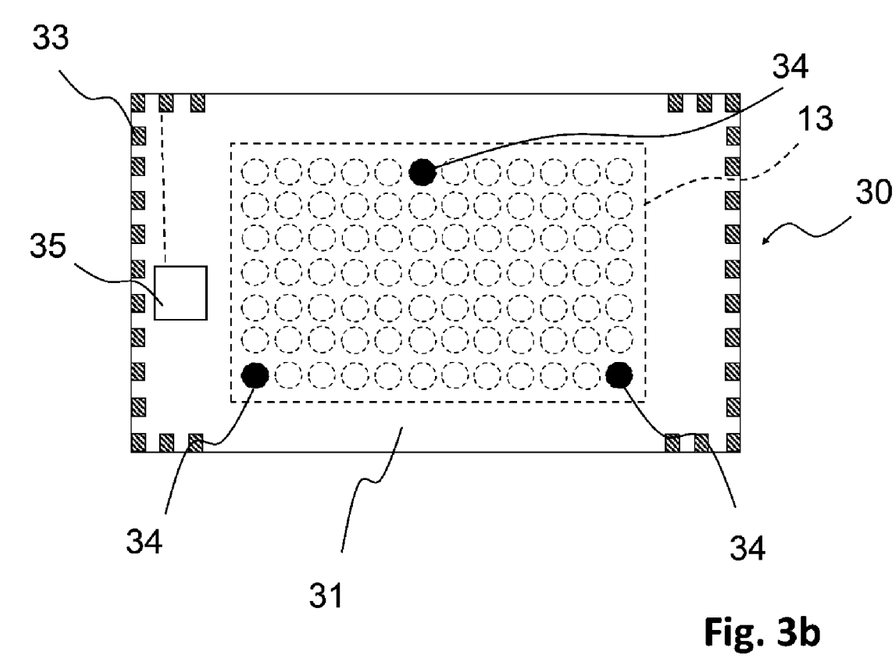
FIG. 3b shows a top view schematic illustration of the UV module according to the first exemplary embodiment.

Shown in FIG. 3*a* is a first exemplary embodiment of a UV module 30 in a side view, and in FIG. 3*b* in plan view. It has a carrier 31, for example made of plastic, whose geometric shape and dimensions are selected such that the UV module 30 can be inserted instead of a microtiter plate into the sample chamber of the thermocycler 1 as it is shown in FIGS. 1 and 2.

It should be mentioned here that an entirely analogously designed UV module can also be inserted into a sample chamber of a qPCR thermocycler, because the sample spaces and heating modules of qPCR thermocyclers are typically quite similar and designed according to the same principles as those of the thermocycler 1 shown here in FIGS. 1 and 2. In addition, qPCR thermocyclers have means for performing optical measurements on the samples contained in the microtiter plate. This requires, among other things, that the sample chamber be designed to be light-tight. Thus, both in the thermocycler 1 shown here and in conventional qPCR thermocyclers, the sample chamber is designed such that, when the lid is closed, the interior of the sample chamber is shielded from the environment in such a way that no UV radiation can escape from the sample chamber into the environment. The UV module 30 described here can therefore be inserted in the same way into the thermocycler 1 shown in FIGS. 1 and 2 as well as into a modified thermocycler, for example with a manually actuated control mechanism, or into a qPCR thermocycler with a closed sample chamber, in a reliable manner for the deactivation of surfaces in the interior of the sample chamber with UV radiation in the UV-B or UV-C range.

A plurality of UV-LEDs are arranged on the carrier 31 as radiation sources 33 for UV deactivation of the sample chamber. In the present example, the UV-LEDs are arranged on two sides in an edge region of the carrier 31 and point in different directions, so that UV radiation is emitted from the carrier 31 in a plurality of spatial directions. The radiation sources 33 can, for example, be configured to emit UV radiation in a wavelength range between 250 and 280 nm.

The carrier 31 has on one side shaped elements 34 which are designed in such a way that they fit into receptacles of the temperature control block 13 (indicated by dashed lines in FIG. 3*b*) of the thermocycler 1. In the PCR operation of the thermocycler 1 these receptacles serve to accommodate reaction vessels or depressions of the microtiter plate. By means of the shaped elements 34, it is ensured that the carrier 31 can be arranged in a predefined position in the sample chamber of the thermocycler 1 which is correct for UV deactivation.

A control unit 35 is arranged on the carrier 31 and is configured to control, e.g., to activate and/or deactivate, the radiation sources 33 for the emission of UV radiation. For the sake of clarity, the connection of the control unit 35 to the radiation sources 33 is shown in FIG. 3*b* only with a single dashed connecting line between the control unit 35 and one of the radiation sources 33. The control unit 35 may, for example, comprise a logic unit, for example a logic circuit, or a more complex computing unit, for example a microcontroller. It may moreover include a driver circuit for the radiation sources 33. However, the driver circuit can also be formed separately from the control unit 35 and be controlled by said control unit 35.

In order to ensure that the radiation sources 33 cannot be excited inadvertently or improperly to emit UV radiation, e.g. if the UV module 30 has not yet been correctly placed in the sample chamber, the driver circuit can be galvanically separated from its current source. This separation is only canceled by the control unit 35 if it receives at least one information item which indicates to the control unit 35 that the operation of the radiation sources 33 is safe, i.e. that the thermocycler 1 is in an operating state that is safe for the deactivation of the surfaces within the sample chamber. This at least one information item can come from a sensor and/or from the thermocycler 1.

According to an embodiment of the present disclosure described here, the controller of the thermocycler 1, said controller being arranged in the base unit 2 or outside the base unit 2, can form or comprise a logic unit which serves to supply the at least one information item to the control unit 35. The logic unit of the thermocycler 1 may, for example, comprise a circuit arranged on a circuit board. It may comprise a logic circuit based on Boolean algebra, or a more complex computing unit. In the second instance, it can comprise at least one processor, memory elements, and one or more operating programs stored in one or more of the memory elements and executable by the processor.

For example, the logic unit of the thermocycler 1 can be configured to transmit the at least one information item to the control unit 35 only when it registers, with the aid of its internal control data for the lid drive, or on the basis of measurement signals of a sensor which monitors the suitability of the lid 3, that the sample chamber is closed such that no UV radiation can escape from the sample chamber to the outside. A suitable sensor for monitoring the condition of the lid can be a microswitch or a proximity switch, for example. The logic unit may transmit, as the at least one information item, a simple control command to the control unit 35, on the basis of which the control unit 35 switches on the radiation sources 33. It is also possible that the logic unit transmits information for authentication—a password, an identifier, or a security token—to the control unit 35.

Additionally or alternatively, the UV module 30 can have a radiation detector, for example a daylight sensor, for example a photodiode or a photo resistor, which is configured to communicate a measurement signal or a quantity derived therefrom to the control unit 35. On the basis of a comparison of the sensor signal with a target signal or a target measured value which represents the measurement signal of the radiation detector in the completely closed sample chamber, a sensor circuit of the sensor or the control unit 35 can determine whether activating the UV radiation sources is safe. If the condition is met that the measurement signal or the measured value of the radiation detector agrees with the target signal or target value under consideration of a tolerance range, the control unit 35 can activate the radiation sources 33 for the emission of UV radiation. Instead of a radiation detector, other sensors can also be used for the same purpose, insofar as their measurement signal allows a conclusion to be drawn as to whether the sample chamber is properly closed.

It is also possible for the control unit 35 to receive two or more redundant information items from the logic unit of the thermocycler 1 and from at least one further source, for example from the aforementioned radiation detector. In this instance, the control unit 35 is configured to activate the radiation sources 33 only when both information items are present and correspond to a safe operating state of the thermocycler, i.e., in the present instance to a completely closed sample chamber from which no UV radiation can escape to the outside.

A signal according to a Bluetooth, NFC, or RFID standard can serve for transmitting the at least one information item from the logic unit of the thermocycler 1 to the control unit 35. If the logic unit transmits a key or token to the control unit 35 in order to signal that a safe operating state is present, it can also be a mechanical or an electronic key.

For the use case described in the present exemplary embodiment, transmission by means of NFC is especially advantageous since the UV module is arranged only a few millimeters apart from the wall of the sample chamber, so that the short-range NFC technology is well suited for information transmission. This short range is also advantageous in order to prevent an external intervention in the communication between the logic unit of the thermocycler 1 and the control unit 35. Alternatively, communication between the logic unit of the thermocycler 1 and the control unit 35, or else a communication between the aforementioned sensor and the control unit 35, can take place in a wire-bound manner, for example via a cable connection or a flexible circuit board.

For a power supply, the UV module 30 can have a battery, for example, a battery that can be recharged without contact (not shown here). Alternatively, it can also be connected to a power supply of the thermocycler 1 by means of a cable or a flexible circuit board in order to be supplied with power by said power supply.

To dissipate heat from the radiation sources 33, the UV module 30 can have cooling elements, for example Peltier elements. In the present example, however, the cooling is accomplished by means of the temperature control elements of the thermocycler 1. This can take place in the following way: If a deactivation of the sample chamber is to be performed, the thermocycler 1 is put into a decontamination mode, for example by an input of an operator or by a robot controller, and the UV module 30 is inserted into the sample chamber instead of a microtiter plate with samples. In the decontamination mode, the logic unit of the thermocycler 1 first checks, as described further above, whether the device is in a safe operating state, i.e. that the lid 3 is closed, so that no UV radiation can escape from the sample chamber to the outside. The logic unit then transmits to the control unit 35 the at least one information item, which the control unit 35 processes and on the basis of which the control unit 35 activates the radiation sources 33. A timer can be provided which maintains the operation of the radiation sources 33 for a predefinable period of time and deactivates them after the period of time has elapsed. This can be integrated in the control unit 35. With the transmission of the information to the control unit 35, the logic unit of the thermocycler 1 begins the execution of a control program with which a cooling of the radiation sources 33 is performed by means of the temperature control elements of the thermocycler 1, for example, by regulating in reference to a predefined temperature of the temperature control block 13. Advantageously, the UV module can have heat contact surfaces which bear directly and with mechanical contact pressure against the temperature control block (not shown in FIG. 3a or 3b).

The arrangement of the UV-LEDs as radiation sources 33 is shown only by way of example in the exemplary embodiment described here and in FIGS. 3a and 3b. Just like the shape and dimensions of the carrier 31, it can be changed both centrally and marginally, depending on the geometry of the sample chamber and the performance of the LEDs, so that the interior surfaces of the chamber are sufficiently illuminated for the deactivation. A timer can be used to set a suitable radiation dose.

Figure 4A:
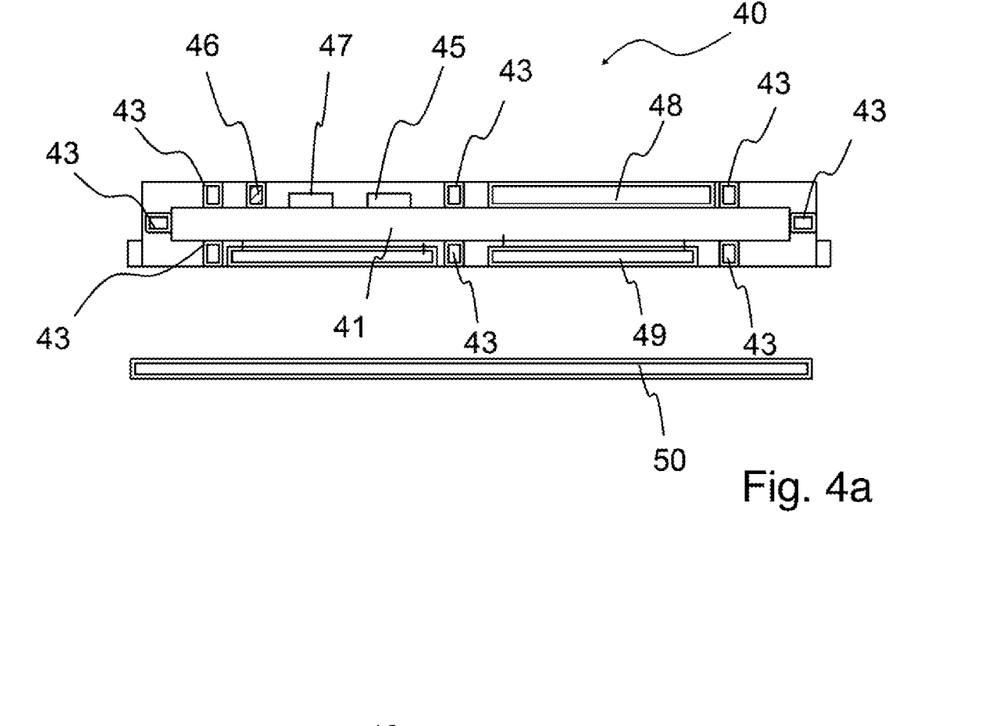
FIG. 4a shows a cross-sectional view schematic illustration of a UV module according to a second exemplary embodiment of the present disclosure.
Figure 4B:
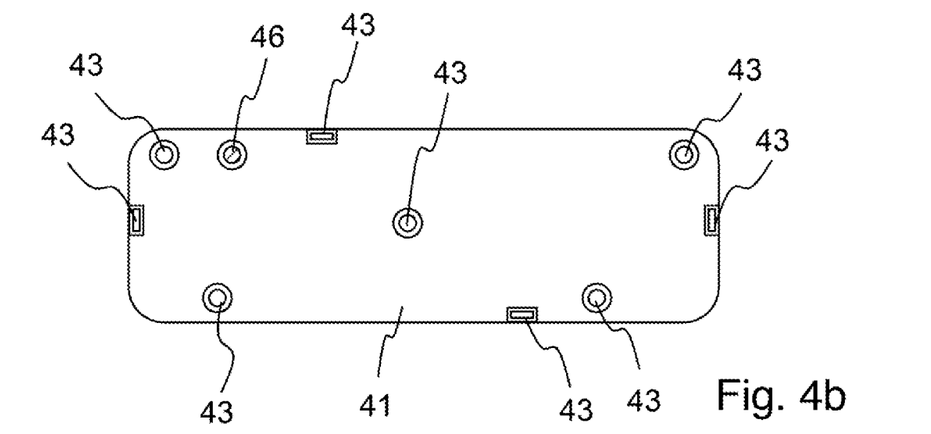
FIG. 4b shows a top view schematic illustration of the UV module according to the second exemplary embodiment.

Shown in FIG. 4a in a longitudinal sectional representation, and in FIG. 4b in plan view, is a second exemplary embodiment of a UV module 40 suitable for deactivating the surfaces of an interior in a device, for example a laboratory device for the examination or treatment of samples containing biological material. The UV module 40 can be introduced into an interior of a device in order to deactivate the surfaces within this interior. It has a carrier 41 which, in the exemplary embodiment shown here, is formed by a printed circuit board. A plurality of radiation sources 43, which in the present example are embodied as UV-LEDs, are arranged on the carrier 41. The UV-LEDs are arranged both on the sides of the carrier 41 and on the top and bottom of the carrier 41, so that they radiate in a plurality of spatial directions when they are excited to emit UV radiation.

The UV module 40 further comprises a processor that serves as the control unit 45 of the UV module. The control unit 45 serves inter alia to excite the UV-LEDs for emitting radiation. Furthermore, a photodiode 46 and a multi-sensor 47 are arranged on the carrier 41 and are connected to the control unit 45 in order for said control unit 45 to receive measurement signals. The multi-sensor 47 may include a temperature, acceleration, and/or position sensor. The control unit 45 is configured to process the measurement signals of the photodiode 46 and of the multi-sensor 47. At least one of the measurement signals can be used by the control unit 45 to control, for example, activate, the radiation sources 43 for emitting radiation, said control being on the basis of the at least one measurement signal.

The UV module 40 moreover has a receiver coil 49 which is arranged on the carrier 41 and serves as a receiver interface via which the control unit 45 can obtain information by means of RFID or NFC. For example, the receiver coil 49 may be coupled for communication to a transmitting coil 50 that is arranged in a wall of the interior of the device to be decontaminated, into which the UV module 40 is inserted. Via the interface formed by the receiver coil 49, the control unit 45 can obtain at least one information item on the basis of which the control unit can excite the radiation sources 43 for the emission of UV radiation.

The carrier 41 is embedded in a frame or a casting so that the surface of the UV module is gap-free and smooth and can thus be easily cleaned by wiping disinfection.

As a safety measure to prevent inadvertent or unauthorized activation, the control unit 45 can be configured, in a manner analogous to the exemplary embodiment described above, to activate the radiation sources 43 only after obtaining information indicating a safe operating state of the device. The control unit 45 can obtain this information from the device via the receiver coil 49.

The photodiode 46 or the multi-sensor 47 may additionally or alternatively be incorporated into the safety concept in that they supply additional information on the basis of which the reliability of the information obtained via the receiver coil 49 can be checked. This can be implemented in the manner of a multi-factor authentication, in that information from multiple sources is used to enable the operation of the radiation sources 43.

The UV module 40 moreover comprises a battery 48 that is rechargeable without contact and arranged on the carrier 41. In an automated laboratory application, it is possible to place the UV module 40, when it is not needed, in a charging station in order to charge the rechargeable battery. To decontaminate a laboratory device, the robot can lift the UV module 40 off the charging station and insert it into the interior to be decontaminated. After the decontamination is concluded, the UV module 40 can be brought back to the charging station.

The present disclosure has been described in detail with reference to the deactivation of a sample chamber of a thermocycler. However, it can also be used similarly and in a very analogous manner in other devices. In device interior spaces which are not completely light-tight in relation to the environment, the deactivation by means of UV radiation can also be carried out in a reliable manner if the housing surrounding the interior is made of a material which is no longer transparent to UV-C radiation or even to UV-B radiation. For example, this is the case with polycarbonate composite safety glass panels. Thus, a UV module such as that shown in FIGS. 4a and 4b can be used in a laboratory scale with sample chamber, in a spectrometer with sample chamber, in an incubator, in a liquid handling system with protective hoods and integrated transport devices, or in an automated warehouse. A logic unit of such a device can be configured, in a manner corresponding very much to as described above for a thermocycler, to transmit to a UV module information which represents a safe operating state of the device, e.g. the closed state of the interior or sample chamber.

In a further exemplary embodiment, an information transmission from one device to the control unit 45 can also take place via a data interface per radio, NFC, or RFID, also via an optical transmission method, for example by means of on-line-of-sight data transmission, for example by means of a modulated red LED to the photodiode 46, which outputs a signal to the control unit 45.

UV modules can be adapted to the specific embodiment of sample spaces or storage spaces and be transported with automatic lift, carriage, stacker, and robot systems. For this purpose, their geometry can be adapted to alternative laboratory containers, for example racks or disposables, for example petri dishes.

In automated applications, the UV module can be introduced via a horizontal movement into the interior to be deactivated. Deactivation along the travel path of the UV module can hereby also be achieved. In order also to reach surfaces that are spaced apart or shadowed by built-ins, the UV module can be moved within the interior.

In a further possible embodiment, the UV module 40 can additionally provide mechanical functionality, for example, in addition to the deactivation functionality described in the preceding. For this purpose, it can have located on the carrier 41 a drive, for example a motor, and at least one manipulator which is operatively connected to the motor, for example a plunger or a tilting mechanism. For example, the UV module 40 can be inserted into a device, or one of the aforementioned closed robot systems, or a closed installation. It can thus take on the additional task of removing a consumable module located in the interior (technical term: consumable), for example a cartridge, from an original position within the interior by activating the drive with connected mechanism.

An example of this is the application in a sample chamber for a method, e.g. digital PCR, which runs in a cartridge. Here, the UV module introduced into the interior can serve to deactivate the sample chamber and/or a cartridge arranged therein in the manner described above via irradiation and, after the deactivation has taken place, to release the cartridge from a locking device by means of the drive via mechanical action, and/or to remove it from an original position.

The invention claimed is:
1. A system comprising:
    a thermocycler having an interior and including a temperature control block therein; and
    a UV module configured to be introduced into the interior of the thermocycler and adapted to deactivate biologically contaminated surfaces in the interior, the UV module comprising:
        a carrier;
        a radiation source affixed to the carrier and adapted to emit UV radiation;
        thermal contact surfaces configured to contact the temperature control block of the thermocycler into which the UV module is introduced, wherein the thermal contact surfaces rest against the temperature control block when the UV module is inserted into the interior, and wherein the temperature control block is configured to cool the radiation source; and
        a control unit connected to the radiation source and configured to receive and process at least one information item as to operate the radiation source to emit UV radiation based on the at least one information item.
2. The system of claim 1, wherein the thermocycler includes a logic unit configured to transmit the at least one information item to the control unit.
3. The system of claim 2, wherein the logic unit is configured to transmit the at least one information item to the control unit when the thermocycler is in a predefined operating state.

4. The system of claim 2, wherein the logic unit and the control unit are connected to one another via wireless communication.

5. The system of claim 4, wherein the wireless communication is according to a Bluetooth, near-field communication, or radio-frequency identification standard, via radio communication or via optical communication.

6. The system of claim 2, wherein the control unit is configured to authenticate the logic unit based on the at least one information item and to switch on the radiation source for the emission of UV radiation only after successful authentication.

7. The system of claim 2, wherein the logic unit is configured to authenticate the control unit and to transmit the at least one information item to the control unit only after successful authentication.

8. The system of claim 2, wherein the at least one information item is transmitted to the control unit in the form of a signal.

9. The system of claim 8, wherein the signal is a digital signal.

10. The system of claim 1, wherein the interior is configured to be closed off after the introduction or by the introduction of the UV module such that no UV radiation can escape from the interior to an exterior environment of the thermocycler.

11. The system of claim 10, further comprising a sensor configured to generate a measurement signal from which whether the interior is closed off can be determined.

12. The system of claim 11, wherein the at least one information item, for the reception and processing of which the control unit is configured to, on the basis thereof, switch on the radiation source for the emission of UV radiation, comprises the measurement signal or information derived from the measurement signal, wherein operating the radiation source includes switching on the radiation source.

13. The system of claim 11, wherein the sensor is disposed in the UV module.

14. The system of claim 1, wherein the UV module comprises at least one sensor, which is at least one of a temperature sensor, a movement sensor, a position sensor, a radiation detector, and a camera, in each case connected to the control unit as to transmit at least one measurement signal, and
wherein the at least one information item, for the reception and processing of which the control unit is configured to, on the basis thereof, switch on the radiation source as to enable emission of UV radiation therefrom, comprises the at least one measurement signal or information derived therefrom, wherein operating the radiation source includes switching on the radiation source.

15. The system of claim 14, wherein the UV module comprises a battery connected to the control unit and/or the at least one sensor as a voltage source.

16. The system of claim 15, wherein the battery connected is rechargeable without physical contact.

17. The system of claim 1, wherein the control unit is further configured to switch on the radiation source for emitting the UV radiation based on the at least one information item.

18. The system of claim 1, wherein the UV module comprises at least one temperature control element configured for heating and/or cooling.

19. A method for deactivating biologically contaminated surfaces in an interior of a thermocycler, wherein the thermocycler includes a temperature control block, the method comprising:
introducing a UV module into the interior of the thermocycler, the UV module comprising:
a carrier;
a radiation source affixed to the carrier and adapted to emit UV radiation;
thermal contact surfaces configured to contact the temperature control block of the thermocycler into which the UV module is introduced, wherein the thermal contact surfaces rest against the temperature control block when the UV module is inserted into the interior, and wherein the temperature control block is configured to cool the radiation source; and
a control unit connected to the radiation source and configured to receive and process at least one information item as to operate the radiation source to emit UV radiation based on the at least one information item;
receiving the at least one information item via the control unit of the UV module;
processing the at least one information item via the control unit and operating the radiation source to emit the UV radiation; and
cooling the radiation source using a temperature control device of the thermocycler, which is in thermal contact with the temperature control block, via the thermal contact surfaces of the UV module.

20. The method of claim 19, wherein the thermocycler comprises a logic unit, and wherein the method further comprises:
transmitting the at least one information item from the logic unit to the control unit, wherein the at least one information item comprises a control command and/or an authentication information.

21. The method of claim 20, wherein the logic unit transmits the at least one information item only when the thermocycler is in a predefined operating state.

22. The method of claim 19, wherein the UV module includes at least one sensor connected to the control unit as to transmit to the control unit a measurement signal as the at least one information item, and wherein the method further comprises:
transmitting the measurement signal of the at least one sensor to the control unit.

23. The method according to claim 22, wherein the control unit receives a first information item from the logic unit and receives a second information item from the at least one sensor, and
wherein the control unit only switches on the radiation source when the control unit determines that the thermocycler is in a predefined operating state based on both the first information item and the second information item using predefined criteria.

24. The method of claim 22, wherein the at least one sensor is at least one of a radiation detector, a movement sensor, a position sensor, a camera, and a temperature sensor.

25. The method of claim 19, wherein operating the radiation source includes switching on the radiation source.

* * * * *